United States Patent [19]

Larsen

[11] Patent Number: 5,050,618
[45] Date of Patent: Sep. 24, 1991

[54] METHOD AND APPARATUS FOR MEASUREMENT OF JOINT STIFFNESS

[76] Inventor: Lawrence E. Larsen, 308 Hamilton Ave., Silver Spring, Md. 20901

[21] Appl. No.: 510,201

[22] Filed: Apr. 17, 1990

[51] Int. Cl.⁵ ............................................. A61B 5/103
[52] U.S. Cl. ...................................... 128/774; 128/782
[58] Field of Search ................................ 128/774, 782

[56] References Cited

U.S. PATENT DOCUMENTS

| | | | |
|---|---|---|---|
| 3,465,592 | 9/1969 | Perrine | 73/379 |
| 4,250,894 | 2/1981 | Frei et al. | 128/774 |
| 4,396,025 | 8/1983 | De Rigal et al. | 128/774 |
| 4,432,376 | 2/1984 | Huszar | 128/774 |
| 4,436,099 | 3/1984 | Raftopoulos | 128/782 |
| 4,461,085 | 7/1984 | Dewar et al. | 33/174 L |
| 4,649,934 | 3/1987 | Fraser et al. | 128/782 |
| 4,682,608 | 7/1987 | De Rigal et al. | 128/774 |
| 4,732,381 | 3/1988 | Skowronski | 272/134 |

OTHER PUBLICATIONS

Lehmann; "Spasticity: Quantitative Measurements as a Basis for Assessing Effectiveness of Therapeutic Intervention"; Jan. 1989; pp. 6–15.

Wright; "Quantitative and Qualitative Analysis of Joint Stiffness in Normal Subjects and in Patients with Connective Tissue Diseases"; 1961; pp. 36–45.

Primary Examiner—William E. Kamm
Assistant Examiner—Scott M. Getzow
Attorney, Agent, or Firm—Laubscher Presta and Laubscher

[57] ABSTRACT

A method and apparatus for body joint rotation and measurement to isolate the joint under test is characterized by imposing movement on one member of the joint in a series of discrete increments, whereupon strain is measured at rest over a predetermined range of motion. Measurement of static force v. displacement at each of a plurality of steps in the angular range provides a quantitative test and evaluation of the elastic component of joint stiffness that resists the applied angular displacement. In this way, a static stress-strain loop is produced for each plane of movement. The static modulus of elasticity is derived by the slope of the stress-strain loop at the extremes of the range of motion.

12 Claims, 6 Drawing Sheets

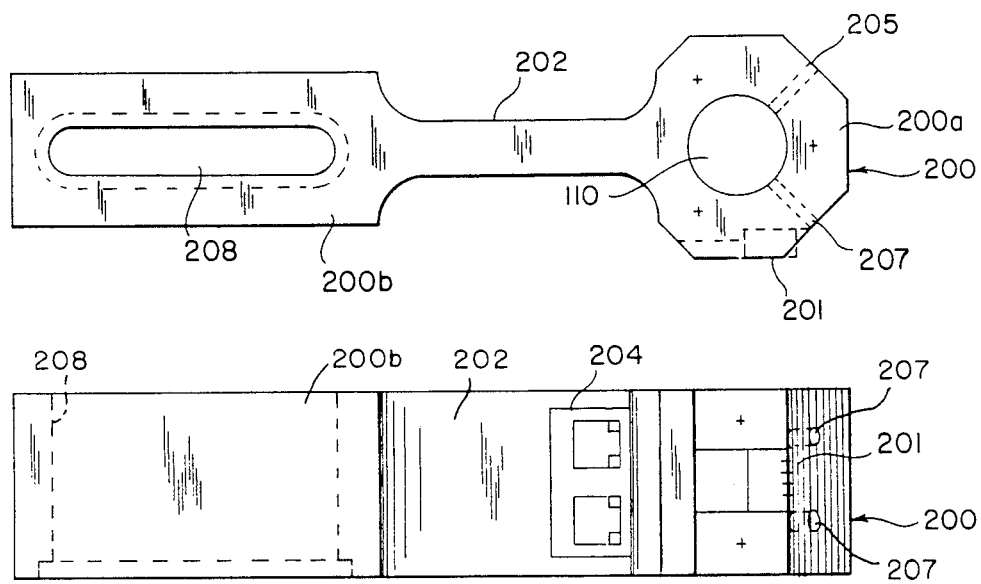
FIG. 6
FIG. 7
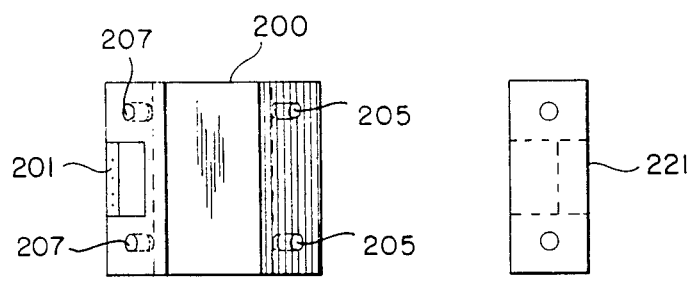
FIG. 8    FIG. 9
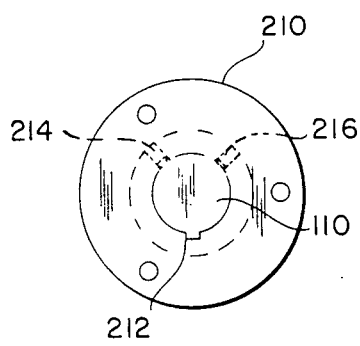 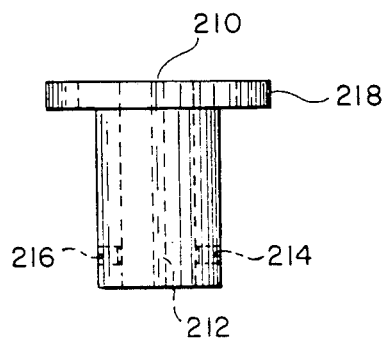
FIG. 10    FIG. 11

METHOD AND APPARATUS FOR MEASUREMENT OF JOINT STIFFNESS

BACKGROUND OF THE INVENTION

The present invention relates to a method and apparatus for quantitative testing and evaluation of body joint stiffness. It is intended for patient evaluation in physical medicine and for objective testing of the efficacy of various therapeutic treatments, such as for example heat and anti-inflammatory pharmaceuticals, to reduce joint stiffness in various disease states such as rheumatoid arthritis, scleroderma, and polymyositis.

Joint stiffness is an important component of rheumatoid arthritis and other connective tissue diseases that, along with pain, largely determine the functional capacity of the patient. Heretofore, joint stiffness was measured in situ by the imposition of continuous sinusoidal motion upon a joint. This method confounds passive and active components of resistance movement. Passive properties include elasticity, viscosity, and friction as components of the resistance to motion in joints. Of these, elasticity is by far and away the most important component (i.e., at least 80%) of the total resistance to movement.

Changes in the passive properties of periarticular structures are of greatest importance to evaluation of rheumatoid arthritis, especially with respect to morning stiffness and prediction of later joint deformity. Active processes, measured concurrently with passive properties of the joint when continuous sinusoidal movement is imposed, largely reflect muscle stretch reflexes. In spastic paralysis, for example, hypertonic stretch reflexes may eclipse the passive properties.

One way to separate passive and active properties in force v. displacement tests of joint movement is to block muscle stretch reflexes with local anesthetics. This procedure is not attractive for routine use. Even in nonspastic subjects, muscle stretch reflexes cannot be noninvasively separated from viscoelastic properties of the joint when the joint is accelerated.

The present invention uses an improved approach based on discrete, rather than continuous, movement wherein strain is measured with the joint stationary at each of several discrete positions within its range of motion. Elastic deformation is avoided as the measurements are taken at a high enough data rate to prevent stress relaxation. This method isolates the dominant passive component (elasticity) of resistance to motion in joints. In this way, objective evaluation of disease response to therapeutic treatments, such as anti-inflammatory agents and heat, may guide treatment regimes to more effectively reduce joint stiffness and relieve pain.

BRIEF DESCRIPTION OF THE PRIOR ART

Various devices are known in the patented prior art for measuring the forces across a body joint. For example, U.S. Pat. Nos. 3,465,592 and 4,732,381 disclose exercise and training devices for measuring body joint forces generated by muscular contraction. U.S. Pat. Nos. 4,436,099 and 4,461,085 disclose goniometers for measuring joint motion. Also known are devices for measurement of viscoelastic properties of tissues as shown for example by U.S. Pat. Nos. 4,432,376, 4,396,025 and 4,682,608.

While the prior devices normally operate satisfactorily, none are capable of measuring resistance to passive motion without muscle stretch reflex in order to determine passive joint stiffness for evaluating disease processes of arthritides and connective tissue diseases that affect periarticular structures.

In order to measure joint stiffness, it is known in the art to apply continuous sinusoidal force to result in motion of the joint and measure passive displacement as a function of driving force over a range of motion. The elastic component of resistance is estimated by determining the slope on the extremes of the stress strain hysteresis loop. The viscous component was determined by the ratio of applied torque to angular velocity, and the friction component was estimated by the second derivative of the loop in its central portion.

Heretofore, the contribution of active muscle properties to such a measurement could not be separated from passive properties of periarticular tissues. Local anesthetic blockade of the stretch reflex is needed, for example. This is a consequence of the fact that data is taken from a torque or strain sensor while the joint is moving. Muscle stretch reflex contribution may be eliminated by resection of the tendons that bridge the joint under study, but this method is of limited value and it removes all effects of the muscle. Passive properties of muscle as well as periarticular tissues are of interest in rheumatoid arthritis and in connective tissue diseases such as polymyositis, polymyalgia, scleroderma, and dermatomyositis where altered biochemical properties are a primary consequence of disease.

In accordance with the present invention, the joint is moved through a small, predetermined, angular increment, stopped, and then stress measurements at rest are taken from a load cell. This cycle is repeated incrementally throughout the desired range of motion. In accordance with the invention, the total passive elastic resistance to motion in a joint is measured, while muscle stretch reflexes and inertial drag intrinsic to the apparatus are avoided.

The prior joint stiffness measurement devices use a variety of push rods, bell cranks, gears and/or pulleys to mechanically connect a continuous drive motor with the subject. This requires repeated mechanical adjustment of the linkage to accommodate changes in the range of motion. The present invention overcomes this drawback by providing a direct driven load cell connected at one end with the drive shaft of the motor and at the other end with the distal member of the joint under test.

In the prior devices, torque sensors are often provided in the linkage to measure the resistance to motion. Consequently, the strain gauge sensors are of a quarter bridge or half bridge design. The present invention on the other hand uses a beam type load cell wherein a full bridge of strain gauges are used, whereby one pair is in extension while the other pair is in compression. This arrangement provides greater signal output to increase noise immunity, cancels temperature effects, and provides immunity to the effects from forces perpendicular to the intended direction.

SUMMARY OF THE INVENTION

The present invention is directed toward an improved method and apparatus for measuring the elastic component of resistance to angular displacement of a body joint between body members. An elongated linkage is provided having one end arranged concentric with the axis of the joint and a second end adapted for connection with one of the body members. A motor is connected with the linkage one end for transmitting incremental angular rotation thereto under control of an automatic control device. Strain gauges are provided on the linkage for measuring the static strain thereof in selected incremental rotational positions throughout the range of angular displacement of the joint in order to produce a strain signal as a function of angular position. A processor calculates the slope of the strain signal in order to determine the elastic component of resistance of the joint as a measure of joint stiffness separate from the combination of elastic properties and muscle stretch reflexes elicited by continuous acceleration of the joint.

A high torque stepper motor is used to move the joint over any multiple of increments. At each angular position, stress is maintained (while static strain is measured) by the holding torque of the motor.

The linkage of the invention is driven directly by the stepper motor. The linkage arm connected between the stepper motor shaft and a fixture that holds the distal portion of the body joint under test also serves as a load cell. The distal attachment is radially adjusted to place the center of joint rotation adjacent to the center of the motor shaft. Then the proximal portion of the joint is stabilized. Thus, the single linkage serves to adjust the center of rotation and to provide strain gauge distention. The joint under test is stabilized as well.

Preferably, the load cell comprises four strain gauges in a full bridge configuration. Thus, two elements are in tension and two are in compression for any deflection of the linkage, whereby distention is measured by a balanced bridge of strain gauges. The full bridge affords greater signal output and noise immunity, intrinsic temperature compensation, more stable calibration factors, and immunity to errors due to Poisson ratio of the linkage.

BRIEF DESCRIPTION OF THE FIGURES

Other objects and advantages of the invention will become apparent from a study of the following specification when viewed in the light of the accompanying drawing, in which:

FIGS. 6, 7, and 8 are top, side, and end plan views, respectively, of a second embodiment of the linkage/load cell according to the invention;

FIG. 9 is a side view of a clamp used with the apparatus of FIGS. 6-8;

FIGS. 10 and 11 are top and side plan views of an insert used with the apparatus of FIGS. 6-8;

DETAILED DESCRIPTION

Figure 1:
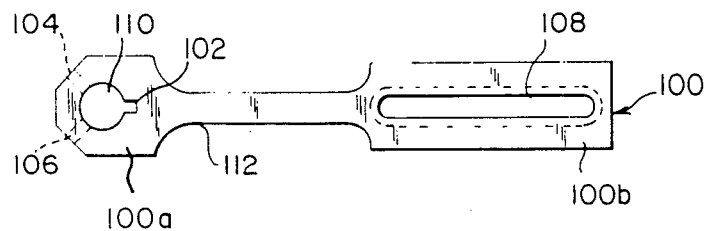
FIG. 1 is a top plan view of the linkage/load cell device of the joint stiffness measurement apparatus according to the invention.

Referring first to FIGS. 1-5, the structure of the linkage/load cell 100 used with the joint stiffness measuring method and apparatus according to the invention will be described. The linkage is formed of a bendable rigid material such as aluminum. It has a first end 100a arranged adjacent the joint whose stiffness is being measured and concentric with the axis of rotation thereof and a second end 100b adapted for connection with one of the body members connected by the joint. For purposes of illustration, the invention will be described in connection with measurement of stiffness of the wrist connecting the hand with the forearm. However, the invention can be adapted for use in measurement of a number of body joints.

The shaft 110 of a drive motor is connected with the first end 100a of the linkage via a key 102. A pair of set screws 104, 106 connect the shaft 110 with the linkage to insure accurate transmission of rotary movement of the shaft to the linkage as will be developed in greater detail below.

Figure 2:
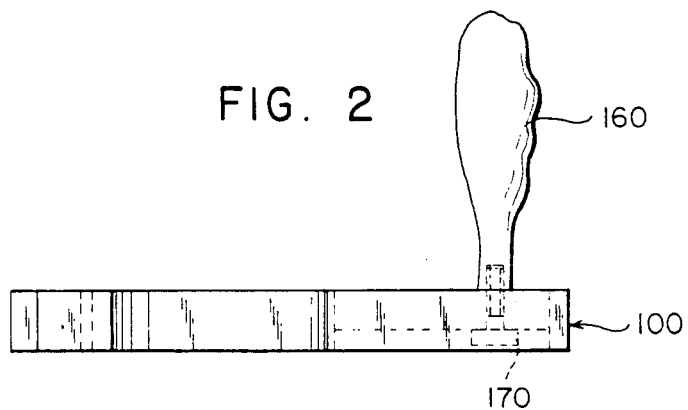
FIG. 2 is a side plan view of the apparatus of FIG. 1 with a first type of handle.

A longitudinal slot 108 is provided in the other end 100b of the linkage. As shown in FIGS. 2 and 4, the slot contains an adjustable fastener 170 with which differently configured handles 160, 180 are connected. The patient grasps a handle (FIG. 3) and, with the fastener loosened, the linkage is adjusted to position the center of rotation of the joint 150 (i.e. the wrist) whose stiffness is being measured over the center of the motor shaft 110. The fastener 170 is then tightened to lock the linkage in the appropriately adjusted condition. Radial adjustment of the attachment point of the linkage to the subject is necessary to position the center of rotation of the shaft 110 over the joint in order to prevent eccentric movement of the joint.

Figure 3:
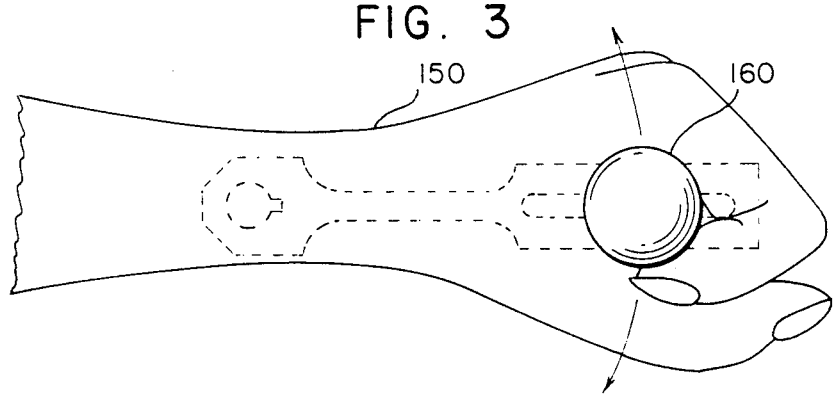
FIG. 3 is a top phantom view of the apparatus of FIG. 2 when used to measure stiffness of the wrist.
Figure 4:
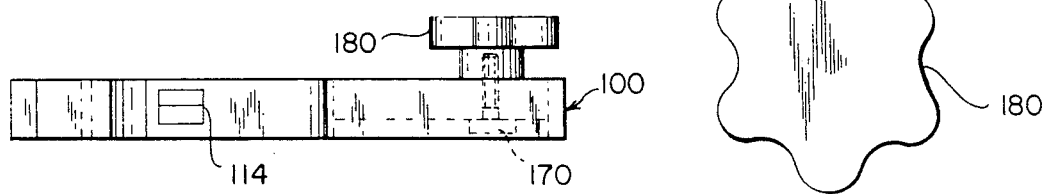
FIG. 4 is a side plan view of a apparatus of FIG. 1 with a second type of handle.
Figure 5:
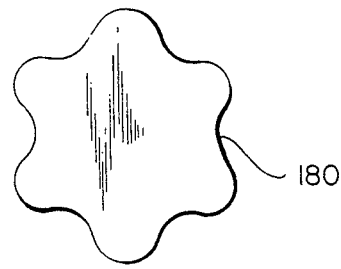
FIG. 5 is a top plan view of the handle of FIG. 4.

The cylindrical handle 160 of FIGS. 2 and 3 is used to test flexion/extension of the wrist. The stellate handle 180 of FIGS. 4 and 5 is used to test abduction/adduction of the wrist.

A load cell 114 (FIG. 4) is connected with the linkage 100 with an adhesive such as cyanoacryllic cement at the proximal end of a section of reduced thickness 112 in order to sense deflection of the linkage. As will be developed below, the linkage is configured as a bending beam whose deflection is measured by the load cell upon operation of the drive motor.

Referring now to the embodiment of FIGS. 6-11, the linkage/load cell 200 is formed from a mechanically dissipative engineering polymer such as DELRIN. As in the embodiment of FIGS. 1-5, the linkage is formed as a beam having a longitudinal area of reduced cross-section 202 and a load cell 204 is connected with the beam adjacent its proximal (first) end 200a. The handle 160, 180 is connected with the distal (second) end 200b of the linkage and a slot 208 is provided to adjust the linkage to the patient by positioning the center of rotation of the joint under test over the center of the shaft 110.

Since the linkage 200 of FIGS. 6-11 is formed of a dissipative polymer, mechanical vibration from the drive motor is quickly dampened within the linkage, thereby reducing ringing in the measured output. However, the choice of a mechanically dissipative material for the linkage requires an aluminum insert 210 for the key way 212 as shown in FIGS. 10 and 11. Set screws 214 and 216 are provided to retain the mechanical connection between the shaft and the joint. The insert 210 is press fit into the linkage 200 and retained therein by set screws (not shown) which pass through openings in the flange 218 of the insert. Clearance holes 205, 207 are provided in the linkage as shown in FIG. 6 to afford access to the screws 214, 216.

The lead wires to the load cell 204 are preferably embedded in the linkage to prevent interference with the joint. A connector 201 (FIGS. 6-8) is provided for the lead wires and a clamp 221 (FIG. 9) holds the connector on the linkage.

Figure 12:
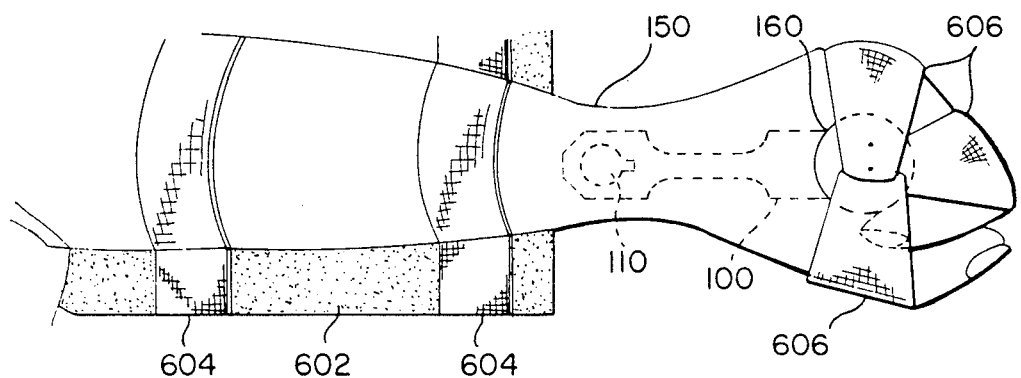
FIGS. 12 and 13 are top and side views, respectively, of the apparatus illustrating the manner with which the device is connected with the patient for measuring stiffness of the wrist joint.
Figure 13:
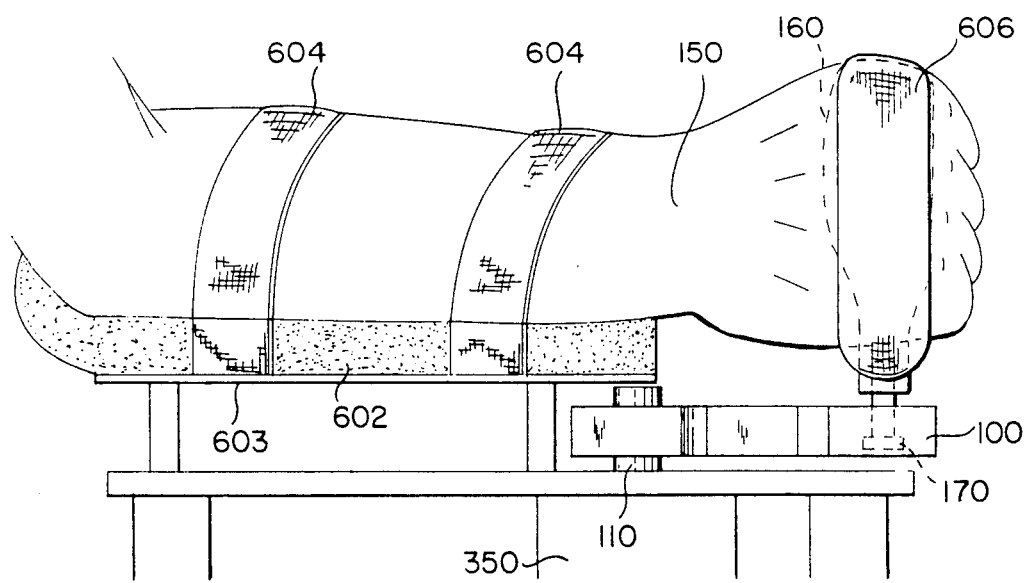

FIGS. 12 and 13 illustrate how the joint under test is stabilized. The proximal portion of the joint is fixed by a conformable pad 602 and elasticized straps 604 over the forearm. The pad extends over the elbow to prevent longitudinal movement, whereas the straps and table 603 provide stability in the other two planes. The distal portion of the joint, i.e. the hand, is attached to the handle 160 (in this case with the palm vertical) and thus to the linkage/load cell 100 for rotation by a stepper motor 350. The distal (i.e. moving) portion is held to the handle by additional elasticized straps 606 for the hand. Similar attachment of the hand for the stellate handle 180 tests the joint in abduction/adduction.

Figure 14:
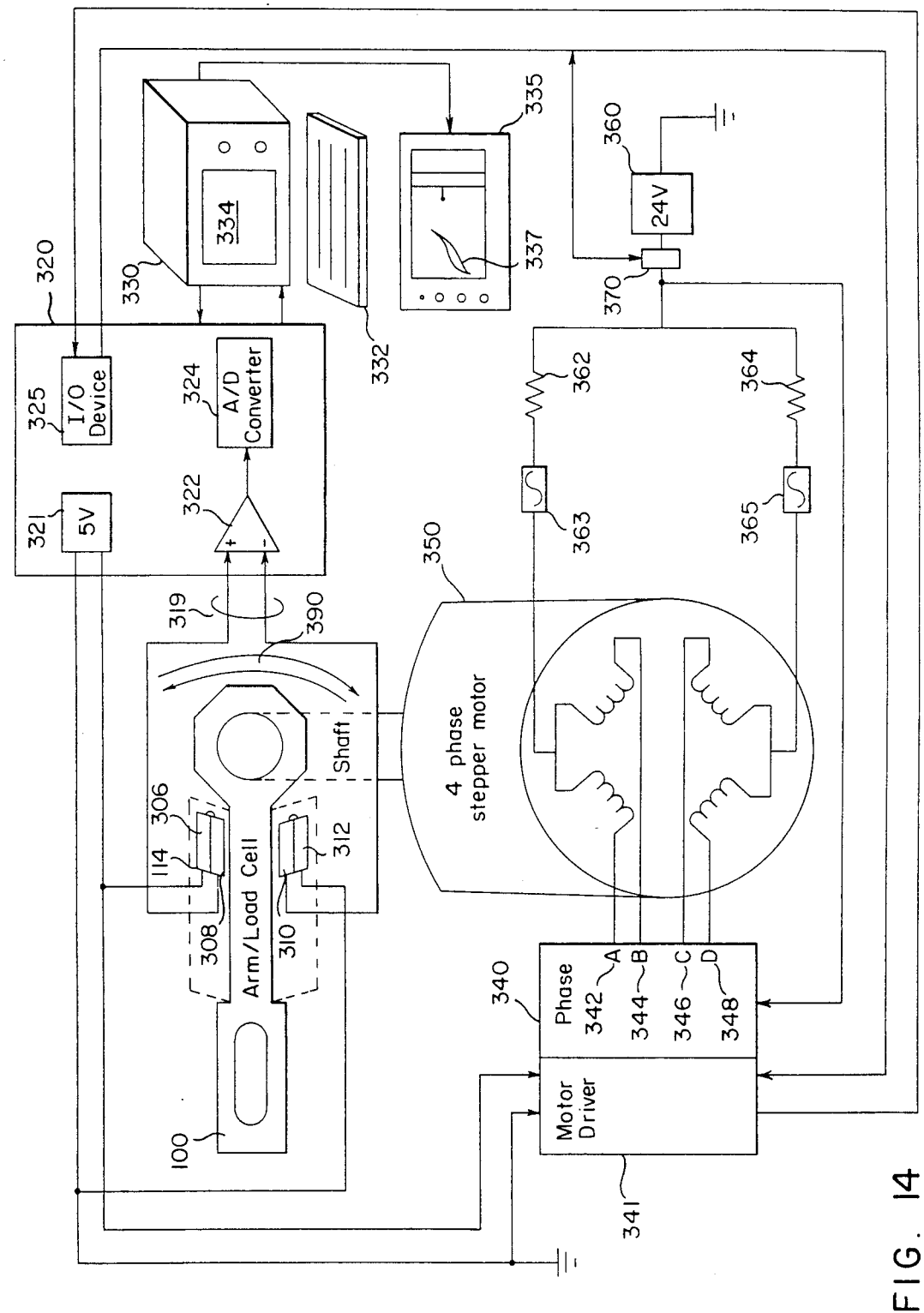
FIG. 14 is a schematic illustration of the joint measurement system according to the invention.

Referring now to FIG. 14, the drive motor and control system for the joint stiffness measuring method and apparatus of the invention will be described. The linkage 100 is shown with the reduced thickness section folded out to illustrate the location of the load cell 114 comprised of four thin film strain gauges 306, 308 in one pair and 310, 312 in the other pair. These are configured as a full bridge with 5V DC energizing voltage from a source 321 derived from the data acquisition interface 320. The bridge output voltage is processed by a differential amplifier 322. The differential voltage is sampled at rest in a plurality of positions by an analog to digital converter 324.

The system is controlled by a personal computer 330 with a data acquisition interface 320 that provides both digital input and output via an I/O device 325, such as an Intel 8055 device, and analog input from the linkage via the differential amplifier 322 which precedes the A/D converter 324.

System software controls the I/O device 325 to provide increment and direction controls to a motor interface 341 of the phase driver 340 for the drive motor 350. A characterizing feature of the invention is that the motor 350 is a stepper motor for rotating the shaft 110 in discrete increments. Rotation of the shaft transmits rotational movement to the first end of the linkage. The strain gauges 306, 308, 310, and 312 measure the static strain of the linkage in selected incremental rotational positions throughout the range of angular displacement of the joint, thereby to produce an analog strain signal 319 which is delivered to the differential amplifier 322 and to the A/D converter 324.

The motor interface 341 drives the 4 phase stepper motor 350 to the predetermined number of steps before the A/D converter 324 samples the output voltage (i.e. the strain signal) from the strain gauge bridge. After the analog value of the stress induced strain signal is sampled by the A/D converter the stepper motor is moved again. In order to compensate for stress relaxation, measurement of static strain is delayed for a small period of time following incremental rotation of the joint by the stepper motor.

In a specific embodiment for wrist testing, the minimum step size is 0.9 degrees. The 4 phases A, B, C and D denoted by 342, 344, 346, 348, respectively, act to move and stop the stepper motor according to full step or half step selection by the interface 341. The coils of the motor are supplied current from a 24V DC power supply 360 via current limiting resistors 362, 364 and fuses 363, 365. The value of the current limiting resistors is set by the peak current device and motor coil impedance as known by those skilled in the art. Temperature rise of the current limiting resistance may be reduced by a switch 370 in the power supply line to apply voltage only when data is actually taken. Chopper type motor controllers do not require these high wattage resistors. Counts of the number of steps, compared to that entered by the operator via a keyboard 332 are used to set the total range of movement shown by the arrows 390 of FIG. 14. The result of the sequence of events described above is to yield a plot of static strain as a function of stress. As is known to those skilled in the art, this plot 337 resembles a hysteresis diagram corresponding to joint position on the abscissa and static strain on the ordinate. A hard copy of the plot is produced on a graphic printer/plotter 335 and displayed on CRT 334.

A number of data samples may be averaged to reduce noise. The cycle of motor commands, to impose stress, followed by conversion of bridge output voltage to measure strain is repeated over the desired range of motion under program control. The strain data as a function of angle (i.e., number of stepper motor steps or time if a fixed step rate is used) is presented as a bivariate display. Bit mapped or graphic images are provided in hard copy by a graphic printer/plotter.

The automated system is used to perform calculations upon the data so collected to insert calibration factors (e.g., strain gauge factors) and to perform error correction (e.g., subtraction of input offset voltage) for the stress-strain loop and to calculate the elastic stiffness of the joint under test at or near the end of the range of motion by analysis of slope in the stress-strain loop.

Figure 15:
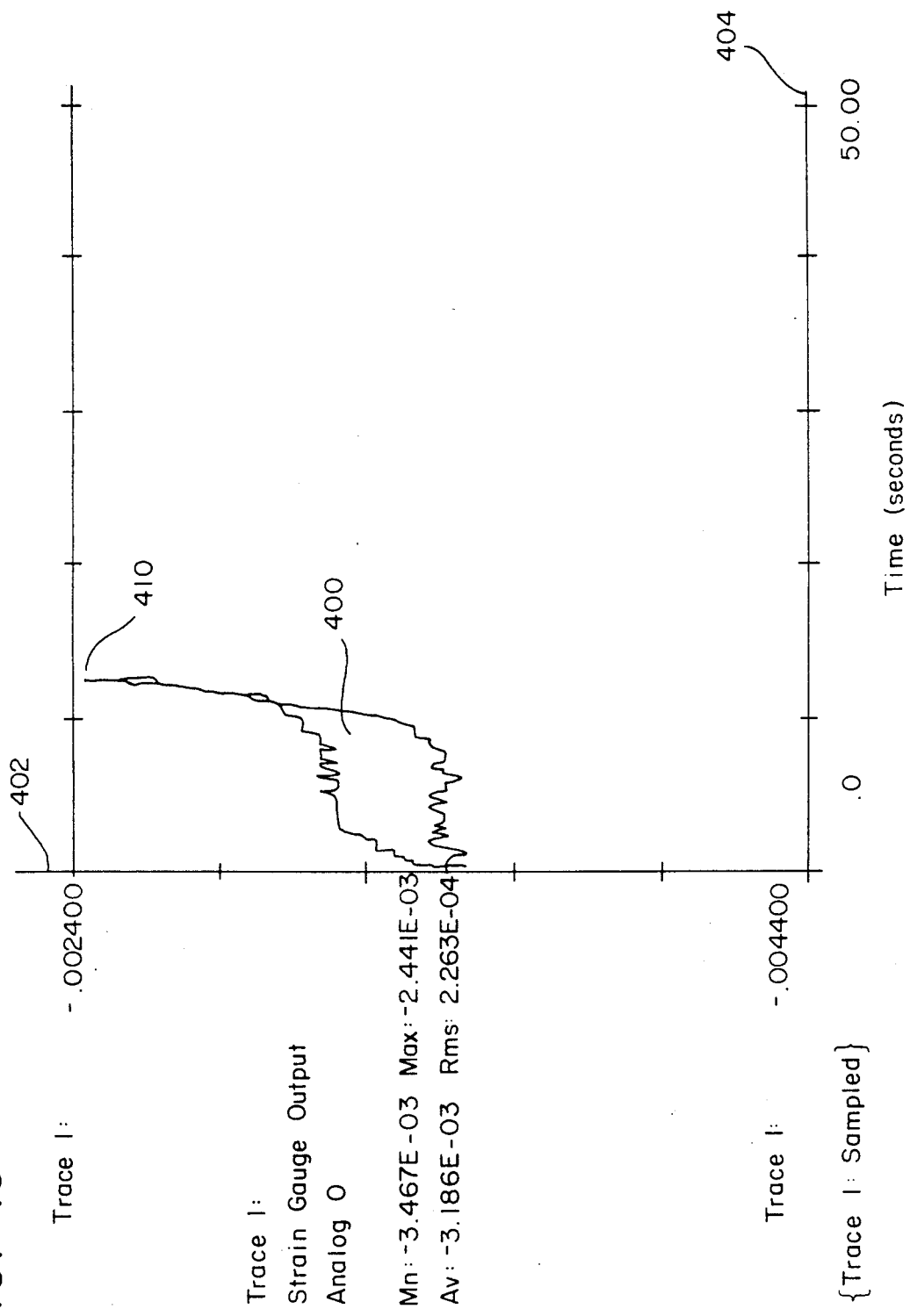
FIG. 15 is a graphical representation of the strain output signal measured by the apparatus of FIG. 12.

FIG. 15 shows the details of the stress-strain loop for a wrist in adduction/abduction. The palm is horizontal with the fingers held within the flutes of the disk-type handle 180 of FIGS. 4 and 5. The lower trace moves to full adduction (movement toward the ulna) to a peak in strain. The ordinate 402 is displayed in millivolts. The DC offset represents input offset voltage of the operational amplifier used prior to A/D conversion. Amplifier input offset voltage and bridge imbalance can be removed by trimming potentiometers as is known to those skilled in the art.

A strain gauge calibration factor, k, (nominally 2 for copper constantine and thin film gauges) is substituted into the following formula to derive absolute values for the strain:

$$V_o = V_i \{ B(k/4) \uparrow e_1 \uparrow \} [G]$$

where $V_o$ is the output voltage, G is the differential gain, $V_i$ is the input or excitation voltage, B is the bridge factor (in this case, B=4 for a full bridge bending beam), k is the gauge factor, and $\uparrow e_1 \uparrow$ is the longitudinal strain value (normalized change in length of the thin film element) for each of the four strain gauges. The absolute values are assumed to be equal. The sign convention adopted is positive strain for tension and negative strain for compression. The result is $$V_o = V_i [4(2/4) \uparrow e_1 \uparrow] [G]$$

or, in terms of strain for a specific value of k $e_1 = \{V_o/V_i [2.08]\}/G.$

Assuming that the bridge is balanced, a typical value for the normal human wrist at 70° flexion is $e_1 = [(1.2 \times 10^{-3})/5] [2.08] = 499$ microstrains.

The measured values of strain may be related to stress (force per unit area) for simple structures. In the case of a bending beam fixed at one end, $F = \uparrow e_1 \uparrow Y\ W_b/4\ G\ L_x$ where Y is Youngs modulus of the beam material, $W_b$ is the section modulus where $W_b = [w\ h^2]/6$ and $L_x$ is the length from the center of the strain gauge grid pattern to the load point. In practice, since the beam cross section is not uniform, a calibrated force is applied in a direction tangential to the arc of movement to the slot, 108 or 208, at various radii from the shaft center 110 while the motor shaft is clamped by the holding torque of the motor 350. The known force and radius provide calibration torque for the load cell from the computer.

FIG. 15 illustrates a typical output indication 400. This is a bivariate plot of force on the ordinate 402 and displacement on the abscissa 404 over the selected range of motion. The data shown covers a range of motion determined by the number of steps per sample (2 steps/sample in this case), the step size (0.9 degree), the sample rate (5 Hz) and the number of samples (62) to yield 75 degrees of adduction followed by an equal movement in abduction. The strain values are highest at the extreme 410 of adduction.

Figure 16:
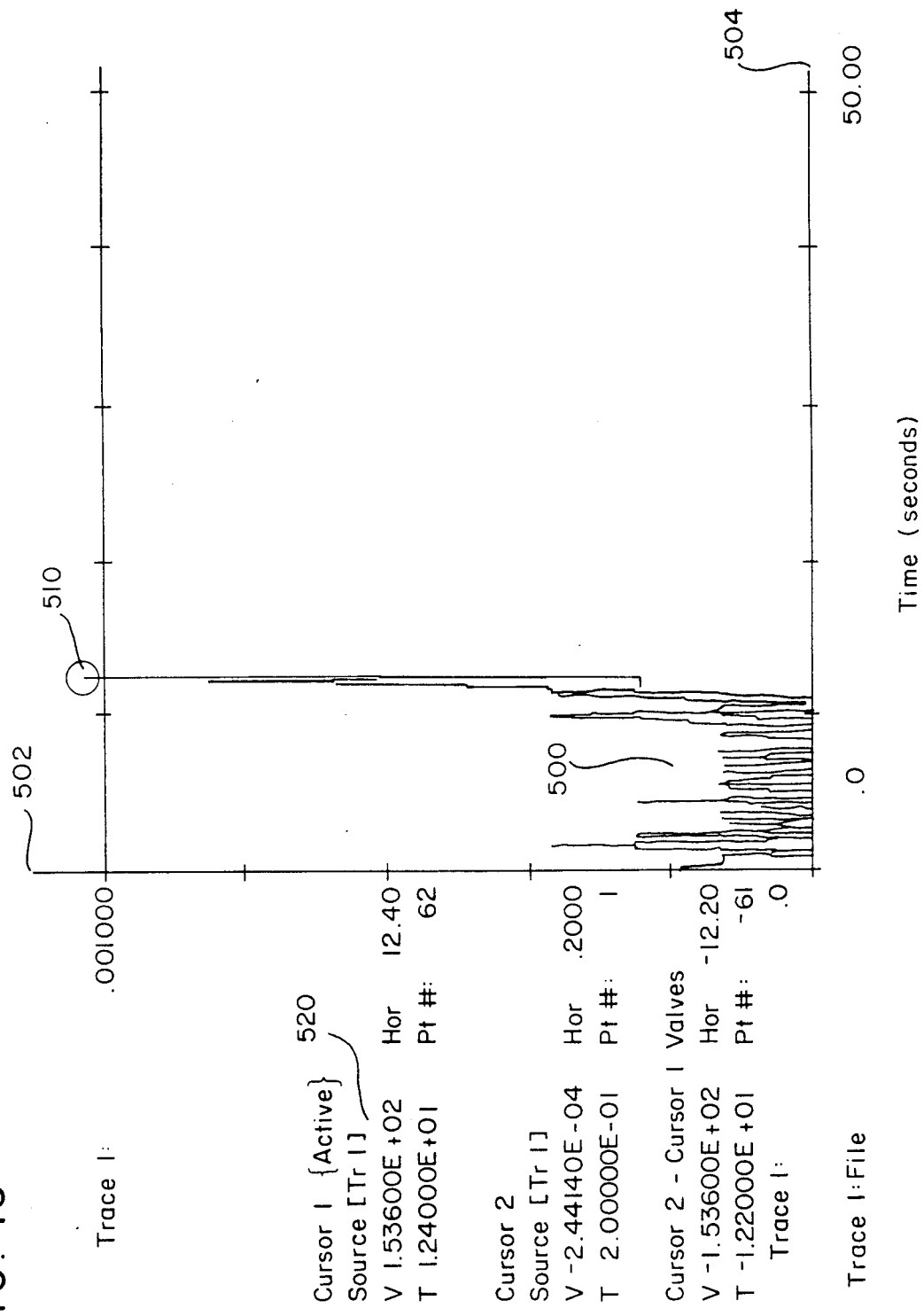
FIG. 16 is a graphical representation of the strain output signal of FIG. 13 following processing.

FIG. 16 is a processed version of the data shown in FIG. 15. The elastic stiffness, Youngs modulus, has been defined above as the ratio of stress to strain. The slope of the data in FIG. 15 calculated at each point is displayed per 500. The ordinate 502 is the value of the slope. The abscissa 504 is the angular position. (For a fixed rate of steps, this is encoded by time). Each point is an instantaneous measure of Youngs modulus. The maximum data value 510 is so extreme that the display has been windowed to show all but the extreme value. The maximum slope is printed as the value (153.6) of the vertical co-ordinate 520 for the active cursor located at data Point No. 62 corresponding to 510.

Alternatively, the last ten points of the stress-strain loop may be fit with a linear function that minimizes the RMS value of the residuals. This process, when applied to repeated tests of the same joint for the same subject, yields consistent data as described below. A comparison of the slopes at the extreme of the range of movement before and after dielectric heating does disclose the therapeutic action of heat to reduce the slope of the stress strain loop.

Preliminary tests of the apparatus of the invention confirmed a system RMS noise value of 7.185 microvolts. This provided an electronic signal to noise ratio of about 40 dB. Bridge balance of 0.00512 was achieved.

The large values of slope of the stress-strain loop at the end of the range of movement confirm the dominant contribution of elastic component of joint stiffness. Tests for reproducibility of elastic stiffness values for the wrist in flexion/extension yielded a mean value of 229 micro-modulus with a variance of 21.79 micro-modulus. In this case, the slope was computed as a least squares, linear fit for the last 10 data points of extension.

Since the volar antebrachial flexors limit wrist extension, dielectric heating (915 MHz, 20 W/20 min. followed by 30 W/29 min.) was applied to the muscle tendon junction. After the 20 W trial with dielectric heating, the slope decreased to 113.9; whereas after the 30 W trial, the slope decreased to 97.6, both compared to an initial value of 229.

In another heat trial for wrist extension, the muscle belly was heated. No change in slope from the range of baseline values was detected. Likewise a test for reduced maximum strain value after heat did not produce a significant difference.

The maximum strain values were remarkably consistent. If the mean value of the loop is subtracted from the maximum strain to accommodate the input offset voltage, the mean value of nine runs on the same subject for a 70° wrist extension was 1085 micro-strain. The variance was 110 micro-strain. There is no evidence that repeated tests on the same subject reduce the maximum strain value.

The baseline tests for maximum strain values of the wrist in abduction/adduction gave an average value of 1377 micro-strain with a variance of 56 micro-strain. After dielectric heating of the wrist at 915 MHz, the maximum strain values for 3, 6, and 12 min. post 25 W/20 min. were 1439 micro-strain, 1075 micro-strain, and 871 micro-strain, respectively.

Baseline slopes from the least squares, linear fit to the last 10 points on adduction were 286.5 micro-modulus with a variance of 13 micro-modulus. After heating, the slopes for 3, 6, and 12 min. were 219.7 micro-modulus, 223.8 micro-modulus, and 187.2 micro-modulus, respectively.

The present invention is a significant improvement over prior joint stiffness measurement techniques. With the apparatus of the invention, displacement is immediately available from counts of the number of steps. In the preferred embodiment, the step accuracy is 3% per step and the step size is 9/10 degree. Thus, the accuracy is better than 3/100°. This greatly exceeds the precision of simple shaft encoders, such as linear potentiometers, where the accuracy is often no better than 1% of full range or 1.8° for a semicircular range of movement. Furthermore, the cost of stepper motors and their associated drivers is far lower than that of DC servo motors/controllers. Furthermore, the single motor linkage of the invention provides strain gauge distention in the order of one part per thousand for typical joints under test due to strain gauge mounting in a region of reduced modulus.

While in accordance with the provisions of the patent statute the preferred forms and embodiments have been illustrated and described, it will be apparent to those of ordinary skill in the art that various changes and modifications may be made without deviating from the inventive concepts set forth above.

What is claimed is:

1. Apparatus for measuring the elastic component of resistance to angular displacement of a body joint between body members, comprising
   (a) means for incremental angular rotation of the joint, including
      (1) an elongated linkage having one end arranged concentric with the axis of the joint and a second end adapted for connection with one of said body members;

(2) drive means connected with said linkage one end for transmitting incremental angular rotation thereto; and (3) means connected with said drive means for controlling the operation thereof;

(b) means connected with said rotation means for measuring the static strain of said linkage in selected incremental rotational positions throughout the range of angular displacement of the joint, thereby to produce a strain signal as a function of angular position; and (c) processing means connected with said measuring means for calculating the slope of said strain signal to determine the elastic component of resistance of the joint as a measure of joint stiffness.

2. Apparatus as defined in claim 1, wherein said drive means comprises a stepper motor.

3. Apparatus as defined in claim 2, wherein said stepper motor includes at least four phases controlled by said control means.

4. Apparatus as defined in claim 1, wherein said linkage comprises a bending beam and said measuring means comprises a load cell mounted on said beam.

5. Apparatus as defined in claim 4, wherein said load cell comprises a plurality of strain gauges for measuring deflection of said beam in said selected rotational positions.

6. Apparatus as defined in claim 5, wherein said strain gauges are matched for resistance and longitudinal strain constant prior to rotation of said first end by said drive means.

7. Apparatus as defined in claim 6, wherein said strain gauges comprise thin film devices mounted on said load cell in a section of reduced beam modulus adjacent to said first end.

8. Apparatus as defined in claim 7, wherein said processing means calibrates and corrects the strain measured at said selected positions.

9. A method for measuring the elastic component of resistance to angular displacement of a body joint between body members, comprising the steps of (a) stabilizing one body member of the joint;

(b) applying a measuring device to the joint with one end of said device arranged concentric with the joint axis;

(c) incrementally rotating said measuring device one end to displace one of the body members relative to the other;

(d) measuring the static strain within said measuring device as a function of stress at selected incremental rotational positions throughout the range of angular displacement of the joint, thereby to produce a static stress-strain loop over a range of motion; and (e) calculating the slope of said static stress-strain loop to determine the elastic component of resistance of the joint as a measure of joint stiffness at the extremes of the range of motion.

10. A method as defined in claim 9, and further comprising the steps of calibrating and correcting the strain measured at said selected positions.

11. A method as defined in claim 10, and further comprising the step of compensating for stress relaxation.

12. A method as defined in claim 11, wherein compensation is performed by delaying the measurement of static strain following incremental rotation.

* * * * *